United States Patent
Scheuermann

(10) Patent No.: US 8,071,155 B2
(45) Date of Patent: Dec. 6, 2011

(54) MEDICAL DEVICES AND METHODS OF MAKING THE SAME

(75) Inventor: Torsten Scheuermann, Munich (DE)

(73) Assignee: Boston Scientific SciMed, Inc., Maple Grove, MN (US)

( * ) Notice: Subject to any disclaimer, the term of this patent is extended or adjusted under 35 U.S.C. 154(b) by 82 days.

(21) Appl. No.: 11/122,583

(22) Filed: May 5, 2005

(65) Prior Publication Data

US 2006/0251794 A1    Nov. 9, 2006

(51) Int. Cl.
*B05D 3/06* (2006.01)
*A61F 2/06* (2006.01)

(52) U.S. Cl. ...... 427/2.1; 427/2.24; 427/2.25; 623/1.11; 623/1.12; 623/1.15; 623/1.2

(58) Field of Classification Search .................... 427/2.1, 427/2.24, 2.15; 623/1.11, 1.15, 1.35; 420/466
See application file for complete search history.

(56) References Cited

U.S. PATENT DOCUMENTS

| | | | |
|---|---|---|---|
| 5,195,969 A | 3/1993 | Wang et al. | |
| 5,238,004 A | 8/1993 | Sahatjian et al. | |
| 5,270,086 A | 12/1993 | Hamlin | |
| 5,366,504 A | 11/1994 | Andersen et al. | |
| 5,372,660 A * | 12/1994 | Davidson et al. | 148/421 |
| 5,477,864 A * | 12/1995 | Davidson | 600/585 |
| 5,674,242 A | 10/1997 | Phan et al. | |
| 5,690,670 A * | 11/1997 | Davidson | 606/198 |
| 5,780,807 A | 7/1998 | Saunders | |
| 5,824,056 A | 10/1998 | Rosenberg | |
| 5,895,385 A | 4/1999 | Guglielmi et al. | |
| 6,033,436 A * | 3/2000 | Steinke et al. | 623/1.15 |
| 6,179,867 B1 * | 1/2001 | Cox | 623/1.15 |
| 6,245,104 B1 | 6/2001 | Alt | |
| 6,287,332 B1 | 9/2001 | Bolz et al. | |
| 6,287,336 B1 * | 9/2001 | Globerman et al. | 623/1.3 |
| 6,387,121 B1 | 5/2002 | Alt | |
| 6,409,754 B1 | 6/2002 | Smith et al. | |
| 6,517,888 B1 | 2/2003 | Weber | |
| 6,652,586 B2 * | 11/2003 | Hunter et al. | 623/18.11 |
| 6,676,987 B2 | 1/2004 | Zhong et al. | |
| 6,726,712 B1 | 4/2004 | Raeder-Devens et al. | |
| 6,767,418 B1 * | 7/2004 | Zhang et al. | 148/421 |
| 6,932,930 B2 * | 8/2005 | DeSimone et al. | 264/235 |
| 2002/0004060 A1 | 1/2002 | Heublein et al. | |
| 2002/0043307 A1 * | 4/2002 | Ishida et al. | 148/411 |

(Continued)

FOREIGN PATENT DOCUMENTS

EP    1034751    9/2000

(Continued)

OTHER PUBLICATIONS

Foreman, "Pack Carburizing," Aug. 1991, ASM Handbook, vol. 4, pp. 325-328.*

(Continued)

*Primary Examiner* — Timothy Meeks
*Assistant Examiner* — Cachet Sellman
(74) *Attorney, Agent, or Firm* — Fish & Richardson P.C.

(57) ABSTRACT

Medical devices, such as stents, and methods of making the devices are disclosed. In some embodiments, a method includes diffusing a first element into a first portion of the medical device. The first element includes carbon, hydrogen, nitrogen, oxygen, or combinations thereof. The first portion includes a refractory material.

52 Claims, 1 Drawing Sheet

U.S. PATENT DOCUMENTS

| | | | |
|---|---|---|---|
| 2002/0188345 A1 | 12/2002 | Pacetti | |
| 2002/0198601 A1* | 12/2002 | Bales et al. | 623/23.55 |
| 2003/0003220 A1 | 1/2003 | Zhong et al. | |
| 2003/0045923 A1 | 3/2003 | Bashiri | |
| 2003/0135266 A1 | 7/2003 | Chew et al. | |
| 2003/0163198 A1* | 8/2003 | Morra et al. | 623/11.11 |
| 2003/0185895 A1 | 10/2003 | Lanphere et al. | |
| 2003/0204248 A1 | 10/2003 | Murphy | |
| 2004/0093061 A1 | 5/2004 | Acosta et al. | |
| 2004/0230290 A1 | 11/2004 | Weber et al. | |
| 2005/0033407 A1 | 2/2005 | Weber et al. | |
| 2005/0060021 A1 | 3/2005 | O'Brien et al. | |
| 2005/0070990 A1 | 3/2005 | Stinson | |
| 2005/0131522 A1 | 6/2005 | Stinson et al. | |
| 2005/0192657 A1 | 9/2005 | Colen et al. | |
| 2006/0069424 A1 | 3/2006 | Acosta et al. | |
| 2006/0079953 A1* | 4/2006 | Gregorich et al. | 623/1.15 |
| 2006/0122694 A1* | 6/2006 | Stinson et al. | 623/1.34 |
| 2007/0168016 A1 | 7/2007 | Gronemeyer et al. | |

FOREIGN PATENT DOCUMENTS

| | | |
|---|---|---|
| WO | WO 91/15152 | 10/1991 |
| WO | WO 03/063733 | 8/2003 |

OTHER PUBLICATIONS

ASM Handbook, vol. 4: Heat Treating (ASM International, 1991), pp. 325.

Schetsky, L., "Shape Memory Alloys", Encyclopedia of Chemical Technology (3rd ed.), John Wiley & Sons, 1982, vol. 20, pp. 726.

* cited by examiner

US 8,071,155 B2

MEDICAL DEVICES AND METHODS OF MAKING THE SAME

TECHNICAL FIELD

The invention relates to medical devices, such as stents, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, covered stents, and stent-grafts.

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

SUMMARY

The invention relates to medical devices, such as stents, and methods of making the medical devices.

In one aspect of the invention, a method of making a medical device includes contacting a first element to a first portion of the medical device. The first element can be carbon, hydrogen, nitrogen, and/or oxygen. The first portion includes a refractory material. At least the first portion is heated while the first portion is in contact with the first element.

In another aspect, a method of making a medical device includes contacting a first element to a first portion of the medical device. The first element can be carbon, hydrogen, nitrogen, and/or oxygen. The first portion includes stainless steel. At least the first portion is heated while the first portion is in contact with the first element.

In an additional aspect, a method of making a medical device includes diffusing a first element into a first portion of the medical device. The first element can be carbon, hydrogen, nitrogen, and/or oxygen. The first portion includes a refractory material.

In a further aspect, a medical device includes a first portion including a refractory material and a first element. The first element can be carbon, hydrogen, nitrogen, and/or oxygen. The first portion includes about 251 ppm or greater of the first element.

In a further aspect, a medical device includes a first portion. The first portion includes a first refractory material and a first concentration of a first element. The first element can be carbon, hydrogen, nitrogen, and/or oxygen. A second portion includes a second refractory material and a second concentration of the first element. The first concentration is greater than the second concentration.

The methods and apparatus can include one or more of the following features.

In some embodiments, the first portion includes about 251 ppm or greater (e.g., between about 251 ppm and about 1000 ppm, about 500 ppm or greater) of the first element after being heated.

In certain embodiments, the first portion has a yield strength of about 350 MPa or greater after being heated.

In some embodiments, a second portion of the medical device has a yield strength of about 300 MPa or less.

In some embodiments, the first portion has a maximum strength of about 500 MPa or greater after being heated.

In certain embodiments, the first portion has a Vickers hardness of about 200 or greater after being heated.

In some embodiments, the refractory material is niobium, zirconium, hafnium, molybdenum, osmium, iridium, tantalum, tungsten, titanium, and/or rhenium.

In certain embodiments, a second portion of the medical device is not substantially contacted by the first element.

In some embodiments, a mask is applied to the second portion prior to contacting the first element to the first portion.

In some embodiments, the first portion comprises a proximal end region of the medical device.

In certain embodiments, the first portion comprises a central region of the medical device.

In some embodiments, substantially only the first portion is heated (e.g., using a laser).

In certain embodiments, the first element is in the form of a solid, a liquid, or a gas.

In some embodiments, the first element includes oxygen.

In some embodiments, the refractory material comprises niobium.

In some embodiments, at least the first portion is heated at a partial pressure of about $10^{-5}$ mbar.

In certain embodiments, at least the first portion is heated at a temperature of about 700° C. to about 900° C.

In certain embodiments, the medical device is a stent, a stent-graft, a guidewire, a catheter, a distal protection device, or an abdominal aortic aneurysm repair device.

In certain embodiments, the medical device is heat-treated.

In certain embodiments, multiple first elements are contacted to the first portion.

In certain embodiments, the first and second refractory materials are niobium, zirconium, hafnium, molybdenum, osmium, iridium, tantalum, tungsten, titanium, and/or rhenium.

In some embodiments, the first and second refractory materials have substantially the same composition.

Embodiments may include one or more of the following advantages.

A medical device, such as a stent, can be made with variable and predetermined mechanical properties, such as strength and hardness. As a result, the medical device can be tailored to adapt well to a particular application. For example, a stent can include relatively flexible end regions and a relatively stiff central region. When the stent is deployed, the relatively flexible end regions can abut against healthy vessel tissue, and as a result, risk of harm to the healthy vessel tissue can be reduced. At the same time, the relatively stiff central region of the stent can be sufficiently strong to support the vessel and prevent further damage to the vessel. The methods of making the medical devices can be conveniently performed with good controllability.

As used herein, an alloy is a homogeneous substance including two or more metals or a metal and nonmetal intimately united, such as by being fused together or dissolving in each other when molten.

Other aspects, features, and advantages of the invention will be apparent from the description of the preferred embodiments thereof and from the claims.

DETAILED DESCRIPTION

Figure 1:
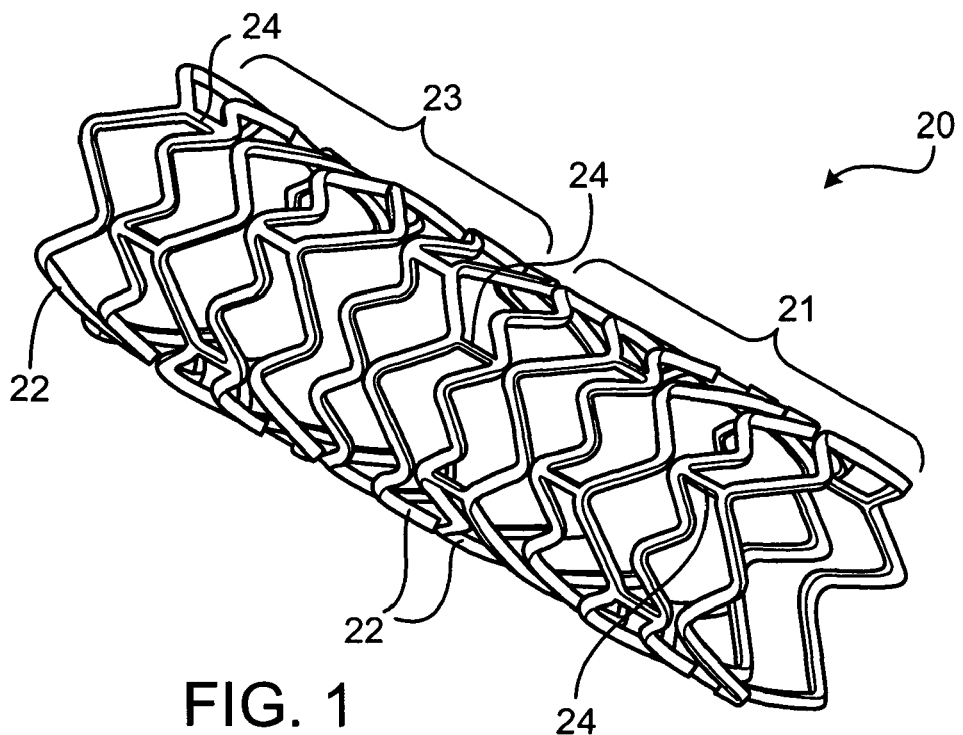
FIG. 1 is a perspective view of an embodiment of a stent.

FIG. 1 shows a stent 20 having portions with different mechanical properties. As shown, stent 20 has the form of a tubular member including a first portion 21 and a second portion 23, each of which is defined by a plurality of bands 22 and a plurality of connectors 24 that extend between and connect adjacent bands. Both portions 21, 23 include a material capable of serving as a matrix in which one or more types of diffusible elements can be dispersed. The material, for example, can be a refractory material (such as a niobium-containing alloy). Portion 21 and portion 23 include different amounts of a diffusible element (such as carbon, hydrogen, nitrogen, or oxygen) that is capable of enhancing the mechanical properties of the refractory material. For example, portion 23 can include trace amounts of the diffusible element, while portion 21 can include greater than about 251 ppm of the diffusible element. As a result, the yield strength, maximum strength, and/or hardness of portion 21 can be greater than those of portion 23. Having variable mechanical properties along the stent can enhance stent performance in certain stent applications. In embodiments in which stent 20 is a renal stent, for example, the relatively stronger portion 21 can be the proximal portion of the stent to secure the stent and to support a renal vessel well. The relatively more flexible portion 23 can be the distal portion of the stent to allow the stent to track a tortuous vessel during delivery and/or to match well with the mechanical properties of the renal vessel.

Stent 20 can include (e.g., be manufactured from) one or more biocompatible materials with mechanical properties that allow the stent to be compacted, and subsequently expanded to support a vessel. As noted above, one or more of the materials from which stent 20 is formed can be capable of serving as a matrix in which diffusible elements can be dispersed. For example, stent 20 can be formed of one or more refractory materials. As used herein, a refractory material is a metal or an alloy having a high melting temperature, for example, greater than about 1750° C. Examples of refractory materials include metals, such as niobium, zirconium, hafnium, molybdenum, osmium, iridium, tantalum, tungsten, titanium, rhenium, and alloys including the metals, such as Ti-6Al-4V, Ti-50Ta, Ti-10Ir, and Nb-1Zr. Other examples of refractory materials include Nitinol (a nickel-titanium alloy), Elgiloy, L605 alloys, MP35N, Co-28Cr-6Mo, Zr-1Nb, Nb-10Ta-10Hf-0.1Y, Nb-10W-2.5Zr, Nb-10Hf-Ti, Nb-30W-1Zr (Cb-1), Nb-28W-2Hf (B-88), Nb-22W-2Hf (VAM-79), Nb-20Ta-15W-5Mo-1.5Zr (Cb-132M), Nb-20W-1Zr (AS-30), Nb-15W-5Mo (F-48), Nb-17W-3.5Hf (SU-31), Nb-9W-3Hf (WC-3009), Nb-11W-3Mo-2Hf (SU-16), Nb-28Ta-10W-0.8Zr (FS-85), Nb-10W-1Zr (D-43), Nb-10W-2.5Zr (Cb-752). Materials other than refractory materials can similarly be used to form stent 20. In some embodiments, for example, stent 20 is formed of stainless steel (e.g., 300 series stainless steel).

The diffusible element(s) can be any material capable of being delivered to the interstices of the material from which stent 20 is formed (e.g., the refractory material) and enhancing one or more mechanical properties of the material of the stent. For example, the diffusible element can increase the hardness, yield strength, and/or maximum strength of the stent material. Without wishing to be bound by theory, it is believed that the diffusible element is capable of blocking the movement of dislocations in the stent material (e.g., the refractory material), thereby increasing its strength and hardness, for example. Examples of diffusible elements include carbon, hydrogen, nitrogen, and oxygen. In some embodiments, more than one type of diffusible element can be used to enhance the strength of stent 20.

The concentration of a diffusible element within a selected portion of a stent can vary as a function of, for example, the particular stent material, the particular diffusible element(s), and/or the targeted mechanical properties. For example, as the concentration of diffusible element(s) in the stent material increases, the strength of the stent material typically increases. As an example, Nb-1Zr diffused with 200 ppm of oxygen can have an ultimate tensile strength of about 280 MPa and a yield strength of about 150 MPa, while Nb-1Zr diffused with about 1,000 ppm of oxygen can have an ultimate tensile strength of about 530 MPa and a yield strength of about 330 MPa. However, when the concentration of the diffusible element(s) within the stent material exceeds a particular level, the stent material can become brittle. For example, an excessively high concentration of the diffusible element(s) within the stent material can cause the stent material to break or fracture without undergoing plastic deformation prior to breaking. In order to prevent Nb-1Zr from becoming brittle, the concentration of oxygen therein can be limited to about 5,000 ppm or less. Similarly, the concentration of hydrogen within Nb-1Zr can be limited to about 500 ppm or less in order to prevent brittleness.

In the embodiment shown in FIG. 1, first portion 21 has a first concentration of a diffusible element that is greater than a second concentration of the diffusible element in second portion 23. First portion 21 can include greater than or equal to about 251 ppm, about 300 ppm, about 400 ppm, about 500 ppm, about 600 ppm, about 700 ppm, about 800 ppm, about 900 ppm, about 1,000 ppm, about 1,500 ppm, about 2,000 ppm, about 2,500 ppm, about 3,000 ppm, about 3,500 ppm, about 4,000 ppm, or about 4,500 ppm of the diffusible element; and/or less than or equal to about 4,500 ppm, 4,000 ppm, 3,500 ppm, 3,000 ppm, 2,500 ppm, 2,000 ppm, 1,500 ppm, 1,000 ppm, about 900 ppm, about 800 ppm, about 700 ppm, about 600 ppm, about 500 ppm, about 400 ppm, or about 300 ppm of the diffusible element. In some embodiments, first portion 21 includes a total of from about 251 ppm to about 5,000 ppm of the diffusible element. Second portion 23 can include about 250 ppm or less (e.g., about 200 ppm or less, 150 ppm or less, 100 ppm or less, or 50 ppm or less) of the diffusible element in some embodiments.

The concentration of the diffusible element can be determined by a targeted enhancement in mechanical properties of the stent material. In some embodiments, the concentration of the diffusible element can be selected to increase the yield strength of the stent material by at least about 50 MPa. For example, second portion 23 can have a yield strength of about 300 MPa or less, and first portion 21 can have a yield strength of about 350 MPa or greater (e.g., from about 350 MPa to about 400 MPa). Alternatively or additionally, first portion 21 can have a maximum strength greater than the maximum strength of second portion 23 by about 50 MPa. For example, first portion 21 can have a maximum strength of about 500 MPa or greater, and second portion 23 can have a maximum strength of about 450 MPa or less. Alternatively or additionally, the difference in Vickers hardness between first portion 21 and second portion 23 can be about 20. First portion 21, for example, can have a Vickers hardness of about 200 or greater (e.g., between about 200 and about 250), and second portion 23 can have a Vickers hardness of about 180 or less.

Figure 2:
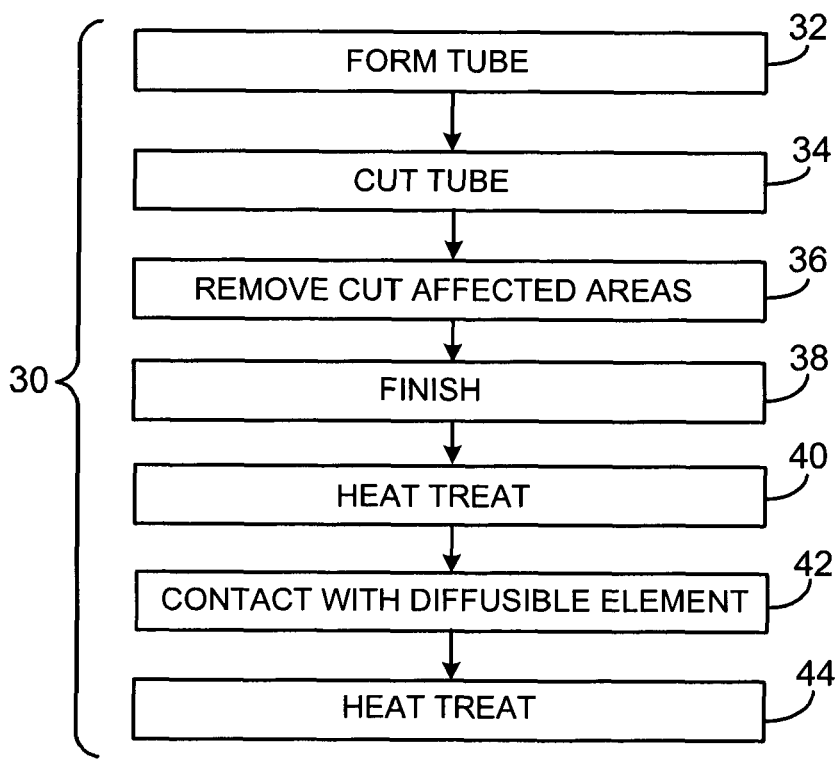
FIG. 2 is a flowchart illustrating a method of making a stent.

Referring now to FIG. 2, a method 30 of making stent 20 is shown. As shown, method 30 includes forming a tube that makes up the tubular member of stent 20 (step 32). The tube is subsequently cut to form bands 22 and connectors 24 to produce an unfinished stent (step 34). Areas of the unfinished stent affected by the cutting are subsequently removed (step 36). The unfinished stent is then finished by, for example, electropolishing (step 38). Next, the stent is heat-treated to produce a small grain structure (e.g., ASTM E112 grain size of about 8 or greater) (step 40). After the heat-treatment, one or more diffusible elements are brought into contact with the stent (step 42). The stent is heat-treated while the diffusible element(s) is in contact with the stent to allow the element(s) to diffuse into the stent (step 44).

As described above, the first step of method 30 includes forming a tube (step 32) that makes up the tubular member of stent 20. The tube can be formed using any of various metallurgical techniques, such as thermomechanical processes. For example, a hollow member (e.g., a rod or a bar) formed of a refractory material can be drawn through a series of dies with progressively smaller circular openings to plastically deform the member to a targeted size and shape. In some embodiments, the plastic deformation strain hardens the member (and increases its yield strength) and elongates the grains along the longitudinal axis of the member. As described below, the deformed member can be heat-treated (e.g., annealed above the recrystallization temperature and/or hot isostatically pressed) to transform the elongated grain structure into an initial grain structure, e.g., one including equiaxed grains. Small or fine grains can be formed by heating the member close to the recrystallization temperature for a short time. Large or coarse grains can be formed by heating the member at higher temperatures and/or for longer times to promote grain growth.

Next, bands 22 and connectors 24 of stent 20 are formed by cutting selected portions of the tube (step 34). The selected portions of the tube can be removed to form bands 22 and connectors 24 by laser cutting, as described in U.S. Pat. No. 5,780,807, which is incorporated herein by reference. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can alternatively or additionally be used, such as mechanical machining (e.g., micromachining), electrical discharge machining (EDM), and photoetching (e.g., acid photo etching).

In some embodiments, after bands 22 and connectors 24 are formed, areas of the tube affected by the cutting operation above can be removed (step 36). For example, laser machining of bands 22 and connectors 24 can leave a surface layer of melted and resolidified material and/or oxidized metal that can adversely affect the mechanical properties and performance of stent 20 (e.g., after heat-treatment). The affected areas can be removed mechanically (such as by grit blasting or honing) and/or chemically (such as by etching or electropolishing).

After the removal of areas of the tube affected by the cutting operation, the unfinished stent is finished (step 38). The unfinished stent can be finished, for example, by electropolishing to a smooth finish. Since the unfinished stent can be formed to near-net size, relatively little of the unfinished stent needs to be removed to finish the stent. As a result, further processing (which can damage the stent) and costly materials can be reduced. In some embodiments, about 0.0001 inch of the stent material can be removed by chemical milling and/or electropolishing to yield a stent.

Still referring to FIG. 2, after the finishing process, the stent is heat-treated (step 40). The stent, for example, can be heated in a furnace at between about 1100° C. and about 1300° C. (e.g., about 1200° C.) for about one hour in order to decrease the grains structure through recrystalization. Alternatively or additionally, the stent can be heated, under vacuum or under a controlled (e.g., inert) atmosphere, in an induction coil, or under a heat lamp. Selected portions of the stent can alternatively or additionally be locally heated. For example, the selected portions can be addressed with a laser, an electron beam, or other focal heating sources, such that the heat is conducted from the addressed portions to the bulk of the tube.

In some embodiments, selected portions of the stent are masked prior to the heat-treatment, such that the unmasked portions experience more heating and grain growth that the masked portions when heated. Upon completion of the heat-treatment, the mask can be removed by, for example, grit blasting, chemical milling, and/or cryogenic fracture.

After the stent has been heat-treated, the diffusible element is brought into contact with first portion 21 of the stent (step 42). The diffusible element can be in the form of a solid (such as powder), a liquid, and/or a gas. Examples of solids including the diffusible element include oxides, such as metal oxides (e.g., niobium oxide and titanium oxide), graphite, and polymers that are capable of decomposing when subjected to heat. Examples of liquids including the diffusible element include water, oils, and saline solutions. Examples of gases including the diffusible element include oxygen, hydrocarbons (such as methane), water vapor, nitrogen (e.g., $N_2/H_2$), and carbon dioxide.

The stent can be contacted with the diffusible element using any of various techniques. For example, the diffusible element, in the form of a liquid or solid, can be applied directly to an outer surface of the stent by spraying, dipping, and/or coating. Alternatively or additionally, the diffusible element, in the form of a gas, can be injected into a chamber in which the stent can be heated. Due to the containment of the gas within the chamber, the outer surface of the stent is in contact with the diffusible element. In some embodiments, similar techniques can be used to bring the diffusible element into contact with other regions of stent 20, such as an inner surface of stent 20.

As described above, the concentration of the diffusible element(s) within the stent material may be dependent upon the targeted physical properties of the stent material. For example, to impart an oxygen concentration of about 1,000 ppm within a 10 mg stent about 10 μg oxygen would be diffused into the stent material. The targeted oxygen concentration can be achieved, for example, by experimenting with one or more test stents to determine a diffusion protocol, and subsequently performing the protocol on similar stents.

Various techniques can be used to create varying physical properties across stent 20. For example, in some embodiments, second portion 23 of the stent is masked prior to applying the diffusible element to the stent. Any of various techniques can be used to mask second portion 23 of the stent. For example, a masking tape can be applied to second portion 23. Thus, as the diffusible element is applied to the stent, it only contacts the unmasked first portion 21. After applying the diffusible element, the masking material can be removed from second portion 23 of the stent so that second portion 23 is exposed for heat-treating. Although both first and second portions 21, 23 of the stent can be subjected to heat-treatment, only first portion 21 includes the diffusible element that can be diffused into the stent material upon undergoing heat-treatment.

Another method of masking second portion 23 includes first placing a removable shield on first portion 21 of the stent. The removable shield can be, for example, an adhesive-backed tape; a dissolvable material (such as a carbon steel that can be dissolved by immersion in an acid such as nitric acid, which can also remove certain recast material formed during manufacturing); or a material (such as gallium metal) that can be melted or sublimed during heat-treatment. The removable shield can include a ceramic and/or a glass that can be removed by heating the tube and allowing differential thermal expansion to separate the shield from the tube. Alternatively or in addition, the removable shield can be removed mechanically, such as by grinding.

Next, a mask is applied over second portion 23 of the stent to serve as an insulative thermal barrier. Examples of masking materials include ceramics (such as titanium nitride, titanium carbide, and silicon carbide), including oxides (such as aluminum oxide, zirconium oxide, and magnesium oxide). The mask can be applied by slurry dipping, spraying, powder coating, photolithographic techniques, printing, physical vapor deposition, sputtering, and/or chemical vapor deposition. After applying the mask, the shield can be removed to expose first portion 21 of the stent. After removing the shield, the diffusible element can be applied to the stent, and then the stent can undergo heat-treatment, as described below.

Second portion 23 can alternatively or additionally be masked using anodization techniques. For example, second portion 23 can be electrically contacted to an anode of an electrochemical assembly to create an oxidation layer on second portion 23, which can provide a function similar to the masking materials discussed above. In some embodiments, the oxidation layer can be heated to diffuse oxygen into the stent to change its mechanical properties.

In addition to the masking techniques described above, other techniques can be used to produce a stent having portions with varying physical properties. For example, unequal amounts of the diffusible element can be applied to portions of stent 20 such that, upon heat-treating stent 20, more of the diffusible element is diffused into some regions of stent 20 than into other regions. For example, in some embodiments, a greater amount of the diffusible element can be applied to first portion 21 than to second portion 23. As a result, first portion 21 has greater strength and/or rigidity than second portion 23 after being heat-treated. For liquid and solid diffusible elements, the amount of diffusible element brought into contact with stent 20 can be determined by the thickness of the layer of diffusible element applied to stent 20, for example.

After bringing the diffusible element into contact with first portion 21 of the stent, first portion 21 is heat-treated (step 44). More specifically, first portion 21 is subjected to heat-treatment while in contact with the diffusible element. As a result of the heat-treatment, the diffusible element diffuses into the refractory material of the stent at first portion 21 to strengthen and/or to harden the refractory material.

Various techniques can be used to heat-treat first portion 21 of the stent. In some embodiments, first portion 21 is heated in a furnace. For example, the entire stent can be heated within a furnace at a temperature of about 700° C. to about 900° C. (e.g., about 800° C.) for about one hour. Although the entire stent is heated, substantially only first portion 21 receives the diffusible element. As a result, the mechanical properties of first portion 21 are affected differently than the mechanical properties of second portion 23. In particular, first portion 21 becomes harder and/or stronger than second portion 23. Alternatively or additionally, only first portion 21 may be inserted into the furnace such that substantially only first portion 21 is heated. In this embodiment, second portion 23 of the stent, which is not in substantial contact with the diffusible element, does not receive the diffusible element to the extent that first portion 21 receives the diffusible element. Thus, after the heat-treatment, second portion 23 has a lower concentration of the diffusible element than first portion 21. As a result, first and second portions 21, 23 can have different mechanical properties and/or characteristics.

As an alternative to or in addition to heating the stent in the furnace, the stent can be heat-treated by addressing the stent with a laser, an electron beam, or other focal heating sources. In certain embodiments, RF or inductive heating techniques can be employed in order to heat the stent. Due to the precision of these heating sources, for example, they can advantageously be used to heat-treat substantially only selected regions of the stent. This allows first and second portions 21, 23 to be in contact with the diffusible element while only heat-treating first portion 21, for example. As a result, the diffusible element is only substantially diffused into first portion 21 of the stent. Deposition of materials and laser heating are described, for example, in commonly assigned U.S. Ser. No. 10/732,492, filed Dec. 10, 2003, and entitled "Medical Devices and Methods of Making the Same," which are incorporated herein by reference.

The amount of diffusible element that is diffused into the stent during the heat-treatment can be a function of heating time and heating temperature. More specifically, the amount of diffusible element diffused into the stent can increase with heating time and heating temperature. Thus, in order to vary the physical properties across the stent, portions of the stent can be subjected to heat-treatment for different periods of time and/or at different temperatures. For example, first portion 21 can be heated for a longer period of time and/or at a higher temperature than second portion 23 such that first portion exhibits greater strength and/or ductility than second portion 23.

In some embodiments, stent 20 (or desired portions of stent 20) is heated at a partial pressure of about $10^{-5}$ mbar or less. As noted above, stent 20 (or desired portions of stent 20) can be contacted with the diffusible element by being placed within a gas chamber filled with the diffusible element (e.g., oxygen) in a gaseous form. In such embodiments, stent 20 can be heated at a partial pressure of about $10^{-8}$ mbar or less. As a result, diffusion of the diffusible element is not substantially caused by the atmosphere alone (e.g., the gas within the gas chamber). Thus, diffusion of the diffusible element can be controlled by the parameters of the heat-treatment (e.g., the heating time and heating temperature).

Stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712, which are incorporated herein by reference. Stents and stent delivery are also exemplified by the Radius® or Symbiot® systems, available from Boston Scientific Scimed, Maple Grove, Minn.

Stent 20 can be of any desired size and shape (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. A renal stent can have a diameter from about 8 mm to about 12 mm. Stent 20 can be balloon-expandable, self-expandable, or a combination of both (e.g., U.S. Pat. No. 5,366,504).

While a number of embodiments have been described above, the invention is not so limited.

As an example, while first portion 21 as described above is the proximal portion of stent 20, in other embodiments, first portion 21 can be formed anywhere along the stent. For example, first portion 21 can be formed at an intermediate portion of a stent or at distal portion of a stent. First portion 21 can include substantially the entire stent to form a hard stent. In some embodiments, a stent can include multiple discrete first portions 21.

A stent having a concentration gradient of diffusible elements can be formed. For example, a stent can include a central portion having a first concentration of a diffusible element, and side portions having a concentration gradient of the diffusible element less than the first concentration. The concentrations can decrease (e.g., linearly) from the central portion to the side portions to provide a stent with a strong central portion and flexible end portions.

Other methods of incorporating diffusible elements can also be used. For example, the diffusible elements can be incorporated using ion beam assisted deposition techniques.

Stent 20 can also be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. Alternatively or additionally, stent 20 can include a ceramic layer, such as iridium oxide, as described in U.S. Pat. Nos. 6,387,121 and 6,245,104.

In other embodiments, the structures and methods described herein can be used to make other medical devices, such as guidewires, a hypotube, catheters, distal protection devices, and abdominal aortic aneurysm repair devices. For example, a guidewire or a hypotube can have a relatively strong and hard proximal end for good pushability, and a relatively flexible distal end for trackability. Similar to stent 20, an abdominal aortic aneurysm repair device can include one or more relatively hard portions and one or more relatively flexible portions for enhanced securement and strength.

The following example is illustrative and not intended to be limiting.

EXAMPLE 1

The following example illustrates a method of enhancing a stent using a diffusible element.

A Nb-1Zr hollow rod having an outside diameter of 2.54 inch and an inside diameter of 2.032 inch is cold drawn through a series of dies in order to form a tubular member of a desired size and shape, and recrystallized (at greater than 1000 degrees Celsius). The series of dies have diameters ranging from 2.5 inch to 0.67 inch, such that the tubular member has an outside diameter of 0.762 inch and an inside diameter of 0.671 inch after being drawn through the smallest die.

Particular areas of the Nb-1Zr tubular member are then laser cut to create multiple bands and connectors, and thereby form the unfinished stent. The unfinished stent is approximately 16 mm in length. Material is removed from selected areas of the unfinished stent using a twelve-watt laser at a frequency of 1.5 kHz for 120 seconds. The laser used to provide the above-noted energy is an Nd:YAG laser, which has a wavelength of 1064 nm. At the same time, a water based lubricant is flowed through the lumen of the tubular member. As the material is removed from the tubular member, the material is carried away by the liquid lubricant.

The unfinished stent then undergoes various chemical treatments to remove dross and to electropolish the stent. In a first dross removal treatment, the stent is exposed to a solution of 33 v/v % $HNO_3$+13 v/v % $HBF_4$ at 65° C. for nine minutes. In a second dross removal treatment, the stent is exposed to a solution of 20 v/v % ABF (ammonium bifluoride)+100 v/v % $HNO_3$ at 37° C. for ten seconds. The stent is then electropolished using 0.5 Ampere for three minutes in a solution of 95 v/v % methanol+5 v/v % sulfuric acid, at −60° C.

After undergoing the above-described chemical treatments, the stent is placed in a furnace that is then heated to a temperature of 1200° C. The partial pressure of oxygen within the furnace is maintained at less than $10^{-8}$ mbar. The stent is heated within the furnace for one hour, cooled to a temperature of 200° C., and then removed.

After the stent has cooled, a masking coating is applied to the outer and inner surface of a distal portion of the stent by dipping. The masking coating is removable by an alcohol based solution.

After applying the masking coating, the stent is placed in a vacuum chamber containing a gaseous mixture of argon and oxygen. The chamber is used for physical vapor deposition and contains a niobium target and a device to sputter Nb atoms on top of the stent surface. On the path from the target to the stent, Nb atoms incorporate oxygen atoms which are deposited onto the stent surface as the compound $Nb_2O_5$. The compound $Nb_2O_5$ is deposited onto the stent until the thickness of $Nb_2O_5$ reaches 200 nm.

The $Nb_2O_5$ contacts the exposed surfaces of the stent and the masking coating. The masking coating is then removed with an alcohol based solution. Due to the removal of the masking coating carrying a layer of $Nb_2O_5$ on its surface, the proximal portion of the stent is contacted by the $Nb_2O_5$ while the distal portion of the stent remains unexposed to the $Nb_2O_5$.

The partial $Nb_2O_5$ exposed stent is again placed into a furnace that is then heated to a temperature of 800° C. The partial pressure of oxygen within the furnace is maintained at less than $10^{-8}$ mbar. The stent is heated in the furnace for one hour. As a result, the proximal portion of the stent has an oxygen concentration of approximately 1000 ppm, and the distal portion of the stent has an oxygen concentration of approximately 250 ppm. After being heated for one hour, the stent is allowed to cool to a temperature of 200° C. and is then removed from the furnace.

All publications, references, applications, and patents referred to herein are incorporated by reference in their entirety.

Other embodiments are within the claims.

What is claimed is:

1. A method of making a medical device, the method comprising:
    applying a layer of solid or liquid material on a first portion of the medical device, the layer of material comprising a first element selected from the group consisting of carbon, hydrogen, nitrogen, oxygen, and combinations thereof, the first portion of the medical device comprising a refractory material; and
    heating the layer of material thereby causing diffusion of the first element into the refractory material,
    wherein, after the layer of material is heated, the first portion of the medical device has a first yield strength and a second portion of the medical device has a second yield strength, the first yield strength being greater than the second yield strength, the first portion of the medical device being laterally spaced from the second portion of the medical device, the medical device being an expandable stent.

2. The method of claim 1, wherein the first portion comprises about 251 ppm or greater of the first element after being heated.

3. The method of claim 2, wherein the first portion comprises about 251 ppm to about 1,000 ppm of the first element after being heated.

4. The method of claim 1, wherein the first portion has a yield strength of about 350 MPa or greater after being heated.

5. The method of claim 1, wherein the first portion has a maximum strength of about 500 MPa or greater after being heated.

6. The method of claim 1, wherein the first portion has a Vickers hardness of about 200 or greater after being heated.

7. The method of claim 1, wherein the refractory material is a material comprising an element selected from the group consisting of niobium, zirconium, hafnium, molybdenum, osmium, iridium, tantalum, tungsten, titanium, and rhenium.

8. The method of claim 1, wherein the second portion of the medical device is not substantially contacted by the first element.

9. The method of claim 8, wherein after heating, the first portion has a first concentration of the first element, and the second portion has a second concentration of the first element different than the first concentration.

10. The method of claim 9, wherein after heating, the first portion comprises about 251 ppm or greater of the first element, and the second portion comprises about 250 ppm or less of the first element.

11. The method of claim 8, further comprising applying a mask to the second portion prior to applying the layer of solid or liquid material to the first portion.

12. The method of claim 1, wherein the first portion comprises a proximal end region of the medical device.

13. The method of claim 1, wherein the first portion comprises a central region of the medical device.

14. The method of claim 1, wherein substantially only the first portion is heated.

15. The method of claim 14, wherein the first portion is heated using a laser.

16. The method of claim 1, wherein the first element comprises oxygen.

17. The method of claim 16, wherein the refractory material comprises niobium.

18. The method of claim 17, wherein at least the first portion is heated at a partial pressure of about $10^{-5}$ mbar.

19. The method of claim 1, wherein at least the first portion is heated at a temperature of about 700° C. to about 900° C.

20. The method of claim 1, further comprising heat-treating the medical device.

21. The method of claim 1, further comprising contacting multiple first elements to the first portion.

22. The method of claim 1, wherein the first yield strength is at least 50 MPa greater than the second yield strength.

23. The method of claim 1, wherein, after heating the layer of material, the first portion comprises about 251 ppm to about 5000 ppm of the first element, and the second portion comprises about 250 ppm or less of the first element.

24. The method of claim 1, wherein the first portion is a proximal portion of the medical device and the second portion is a distal portion of the medical device.

25. The method of claim 1, wherein the first portion is a central portion of the medical device and the second portion is an end portion of the medical device.

26. A method of making a medical device, the method comprising:
    applying a layer of a solid or liquid material on a first portion of the medical device, the layer of material comprising a first element selected from the group consisting of carbon, hydrogen, nitrogen, oxygen, and combinations thereof, the first portion of the medical device comprising a refractory material; and
    diffusing the first element into the first portion of the medical device,
    wherein, after the layer first element is diffused into the first portion of the medical device, the first portion of the medical device has a first yield strength and a second portion of the medical device has a second yield strength, the first yield strength being greater than the second yield strength, the first portion of the medical device being laterally spaced from the second portion of the medical device, the medical device being an expandable stent.

27. The method of claim 26, wherein the first portion comprises about 251 ppm or greater of the first element after diffusing the first element.

28. The method of claim 27, wherein the first portion comprises about 251 ppm to about 1000 ppm of the first element after diffusing the first element.

29. The method of claim 26, wherein the first portion has a yield strength of about 350 MPa or greater after diffusing the first element.

30. The method of claim 26, wherein the first portion has a maximum strength of about 500 MPa or greater after diffusing the first element.

31. The method of claim 26, wherein the first portion has a Vickers hardness of about 200 or greater after diffusing the first element.

32. The method of claim 26, wherein the refractory material comprises an element selected from the group consisting of niobium, zirconium, hafnium, molybdenum, osmium, iridium, tantalum, tungsten, titanium, and rhenium.

33. The method of claim 26, wherein the first element is not substantially diffused into the second portion.

34. The method of claim 33, wherein after diffusing the first element, the first portion has a first concentration of the first element, and the second portion has a second concentration of the first element different than the first concentration.

35. The method of claim 34, wherein after diffusing the first element, the first portion comprises about 251 ppm or greater of the first element, and the second portion comprises about 250 ppm or less of the first element.

36. The method of claim 26, wherein the first portion comprises a proximal end region of the medical device.

37. The method of claim 26, wherein the first portion comprises a central region of the medical device.

38. The method of claim 26, wherein the first element comprises oxygen.

39. The method of claim 38, wherein the refractory material comprises niobium.

40. The method of claim 26, wherein diffusing the first element into the first portion of the medical device comprises applying the first element to the first portion, and heating the first portion.

41. The method of claim 40, further comprising applying a mask to the second portion of the medical device such that the first element is substantially prevented from diffusing into the second portion.

42. The method of claim 41, wherein the mask is applied to the second portion prior to applying the first element to the first portion.

43. The method of claim 26, wherein the first yield strength is at least 50MPa greater than the second yield strength.

44. The method of claim 26, wherein the first portion comprises about 251 ppm to about 5000 ppm of the first element and the second portion comprises about 250 ppm or less of the first element after diffusing the first element into the first portion.

45. The method of claim 26, wherein the first portion is a proximal portion of the medical device and the second portion is a distal portion of the medical device.

46. The method of claim 26, wherein the first portion is a central portion of the medical device and the second portion is an end portion of the medical device.

47. A method of making a medical device, the method comprising:
applying a layer of material on a first portion of the medical device, the layer of material comprising a first element selected from the group consisting of carbon, hydrogen, nitrogen, oxygen, and combinations thereof, the first portion of the medical device comprising a refractory material; and
heating the layer of material at a pressure of about $10^{-5}$ mbar or less thereby causing diffusion of the first element into the refractory material controlled by the parameters of heat treatment,
wherein, after the layer of material is heated, the first portion of the medical device has a first yield strength and a second portion of the medical device has a second yield strength, the first yield strength being greater than the second yield strength, the first portion of the medical device being laterally spaced from the second portion of the medical device, the medical device being an expandable stent.

48. The method of claim 47, wherein the first element is in the form of a solid, a liquid, or a gas.

49. The method of claim 47, wherein the first yield strength is at least 50MPa greater than the second yield strength.

50. The method of claim 47, wherein, after the layer of material is heated, the first portion comprises about 251 ppm to about 5000 ppm of the first element, and the second portion comprises about 250 ppm or less of the first element.

51. The method of claim 47, wherein the first portion is a proximal portion of the medical device and the second portion is a distal portion of the medical device.

52. The method of claim 47, wherein the first portion is a central portion of the medical device and the second portion is an end portion of the medical device.

* * * * *

UNITED STATES PATENT AND TRADEMARK OFFICE
CERTIFICATE OF CORRECTION

| | |
|---|---|
| PATENT NO. | : 8,071,155 B2 |
| APPLICATION NO. | : 11/122583 |
| DATED | : December 6, 2011 |
| INVENTOR(S) | : Torsten Scheuermann |

Page 1 of 1

It is certified that error appears in the above-identified patent and that said Letters Patent is hereby corrected as shown below:

IN THE CLAIMS:

Column 11, Claim 1, Line 15: delete "of" and insert --of a--.

Column 12, Claim 26, Line 38: delete "the layer" and insert --the--.

Signed and Sealed this
Twenty-first Day of February, 2012

David J. Kappos
*Director of the United States Patent and Trademark Office*